United States Patent [19]

Ratton

[11] Patent Number: 5,183,928
[45] Date of Patent: Feb. 2, 1993

[54] PREPARATION OF HYDROQUINONE MONOCARBOXYLATES

[75] Inventor: Serge Ratton, Villefontaine, France

[73] Assignee: Rhône-Poulenc Specialities Chimiques, Courbevoie, France

[21] Appl. No.: 163,196

[22] Filed: Feb. 26, 1988

Related U.S. Application Data

[63] Continuation of Ser. No. 748,454, Jun. 25, 1985, abandoned.

[30] Foreign Application Priority Data

Jun. 25, 1984 [FR] France ............... 84 10184

[51] Int. Cl.$^5$ .............. C07C 67/03; C07C 69/16; C07C 69/28
[52] U.S. Cl. .................................. 560/144
[58] Field of Search .................. 560/144, 109; 260/410.5

[56] References Cited

U.S. PATENT DOCUMENTS 2,588,978  3/1952  Gearhart et al. ............... 560/109

FOREIGN PATENT DOCUMENTS 60092  9/1982  European Pat. Off. .

OTHER PUBLICATIONS

Diana et al., J. Med. Chem., vol. 20, No. 6, pp. 757–761 (1977).
Johnston, Chem. Ind., 1982, p. 1000 TP1 S63.
Olcott, J.A.C.S., vol. 59, pp. 392–393 (1937).

Primary Examiner—Vivian Garner

[57] ABSTRACT

A hydroquinone monocarboxylate, e.g., hydroquinone monoacetate, is facilely prepared by disproportionating/reacting a stoichiometric excess of a hydroquinone dicarboxylate, e.g., hydroquinone diacetate, with hydroquinone, optionally in the presence of a strong acid/transesterification catalyst.

11 Claims, No Drawings

PREPARATION OF HYDROQUINONE MONOCARBOXYLATES

This application is a continuation of application Ser. No. 748,454, filed Jun. 25, 1985, now abandoned.

BACKGROUND OF THE INVENTION

1. Field of the Invention

The present invention relates to the preparation of hydroquinone monocarboxylates from hydroquinone dicarboxylates and, particularly, to the preparation of hydroquinone monoacetate from hydroquinone diacetate.

2. Description of the Prior Art

Hydroquinone monocarboxylates are valuable intermediates for the preparation of monohalohydroquinone (especially monochlorohydroquinone) dicarboxylates, which are themselves useful in the preparation of aromatic polyesters (cf. French Patent Application No. 79/24,135, published under No. 2,465,758 and U.S. Pat. No. 4,118,372). It has been found, in fact, that hydroquinone monocarboxylates may be selectively halogenated to monohalohydroquinone monocarboxylates, in contrast to hydroquinone which gives rise to appreciable amounts of dihalohydroquinone (cf. U.S. Pat. No. 2,743,173), which ultimately are determined as dihalohydroquinone dicarboxylates after acylation. It has also been found that hydroquinone monocarboxylates have the advantage of being capable of being halogenated in the presence of hydroquinone dicarboxylates, which themselves remain essentially inert during the halogenation. Such a property favors the halogenation of mixtures of hydroquinone monocarboxylates, hydroquinone dicarboxylates and minor amounts of hydroquinone, such as those obtained by partial acylation of hydroquinone.

No simple process is known which provides hydroquinone monocarboxylates in and of themselves. A selective route to these compounds from hydroquinone has been proposed, but its complexity deprives it of any industrial interest; in fact, this process consists of protecting one of the hydroxyl groups of hydroquinone as a functional group from which the hydroxyl moiety can readily be liberated, then acylating the other group and, finally, regenerating the first. Such a method has been applied by H. S. Olcott, *J. Am. Chem. Soc.*, 59 392 (1937) to the preparation of hydroquinone monoacetate by reacting hydroquinone with benzyl chlorocarbonate to form the mixed benzyl and p-hydroxyphenyl carbonate which is then acetylated to mixed benzyl p-methylcarbonyloxyphenyl carbonate; in a third stage the latter is subjected to hydrogenolysis in the presence of palladium or platinum. The simplest means for providing hydroquinone monocarboxylates is the partial acylation of hydroquinone, which cannot be produced without simultaneous formation of hydroquinone dicarboxylates [cf. H. S. Olcott, Loc. cit. and D. Johnston, *Chem. Ind. (London)*, page 1000 (1982)]. The use of such mixtures for the preparation of monohalohydroquinone monocarboxylates gives rise to an accumulation of hydroquinone dicarboxylates. The solution to the problem presented by selective production of monohalohydroquinone monocarboxylate and of corresponding dicarboxylates depends, therefore, on the development of a process for the recovery of hydroquinone dicarboxylates and the preparation of hydroquinone monocarboxylates. Cf. U.S. Pat. No. 2,588,978; published European Application, publication No. 0,060,092.

SUMMARY OF THE INVENTION

Accordingly, a major object of the present invention is the provision of an improved process for the preparation of hydroquinone monocarboxylates from hydroquinone dicarboxylates, which improved process features reacting an excess of a hydroquinone dicarboxylate with hydroquinone, optionally in the presence of a catalyst, and which improved process provides both desiderata heretofore conspicuously absent from the state of this art.

DETAILED DESCRIPTION OF THE INVENTION

More particularly according to the present invention, the reaction of hydroquinone dicarboxylates with hydroquinone, hereinafter designated as the "disproportionation reaction" or "disproportionation", may be represented by the following reaction mechanism:

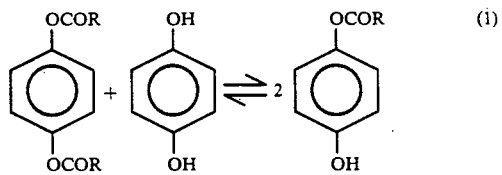

It is an equilibrium reaction which results in the formation of a mixture of hydroquinone monocarboxylate, hydroquinone dicarboxylate and hydroquinone. Its composition depends upon the conditions of reaction. This mixture can be employed for the selective preparation of monohalohydroquinone monocarboxylates by halogenation of the hydroquinone monocarboxylate comprising same. In this case it is important that as little hydroquinone as possible remain in the mixture because, during subsequent halogenation, this compound gives rise to the production of undesirable dihalo derivates. This is the reason why the process is carried out in the presence of an excess of hydroquinone dicarboxylate which enables the reaction equilibrium to be shifted such as to promote the formation of hydroquinone monocarboxylate.

As a general rule, the excess of hydroquinone dicarboxylate is at least 0.5 mole vis-a-vis the stoichiometric amount resulting from the aforesaid reaction scheme (1). There is no critical upper limit on the excess of hydroquinone dicarboxylate; however, beyond a certain value, the advantage obtained in the conversion of hydroquinone is counterbalanced by the disadvantage of having to recycle large amounts of hydroquinone dicarboxylate. Consequently, it is unnecessary to employ an excess of hydroquinone dicarboxylate which is greater than 4 moles relative to the stoichiometric amount. In short, the amount of hydroquinone dicarboxylates, expressed in moles per mole of hydroquinone, is at least 1.5 and preferably in a range of from 1.5 to 5.

The disproportionation reaction may be carried out in bulk or in a solvent, at the temperature of reaction, for hydroquinone dicarboxylates, hydroquinone and hydroquinone monocarboxylates, which is inert under the conditions of the reaction. In the latter case, use is made more especially of:

(i) Carboxylic acids which are liquid under the conditions of the reaction and preferably at ambient temperature; representative are alkanoic acids containing from 1 to 8 carbon atoms, such as formic, acetic, propionic, butyric, isobutyric, 2-methylbutanoic, 2-ethylbutanoic, 2,2-dimethylbutanoic, pentanoic, 2-methylpentanoic, 5-methylpentanoic, 2-ethylhexanoic and hexanoic acids. Preferably used is the carboxylic acid from which the hydroquinone dicarboxylate is derived.

(ii) Aliphatic or heterocyclic ethers, such as ethyl, n-propyl and isopropyl ethers, tetrahydrofuran, and dioxane.

(iii) Saturated aliphatic, saturated alicyclic or aromatic hydrocarbons, such as n-hexane, cyclohexane, toluene or benzene.

(iv) Haloalkanes, such as chloroform, carbon tetrachloride or trichloroethylene.

(v) Haloaromatic hydrocarbons, such as chlorobenzene.

The temperature of the disproportionation reaction can vary over wide limits. In general, temperatures in the range of from 50 to 250° C., and preferably from 80 to 180° C., are suitable. The reaction may be carried out at normal pressure or under pressure; when the temperature selected is above the boiling point of some of the components of the mixture, it is possible to conduct the reaction under the autogenous pressure of the reactants.

When the disproportionation is carried out in a carboxylic acid it is possible to carry out the reaction either in the presence or in the absence of a catalyst. When a catalyst is indeed employed, strong inorganic or organic acids are used therefor, namely, acids which have a pK below 1 in water at 25° C. Preferably used are sulfuric acid and sulfonic acids, such as methanesulfonic, di- and trifluoromethane sulfonic, benzenesulfonic, toluenesulfonic, naphthalene sulfonic acids, or sulfonic resins.

The amount of strong acid, expressed in equivalents of protons per mole of hydroquinone, can also vary over wide limits. Typically it ranges from 0.0001 to 0.2 equivalent of proton per mole of hydroquinone.

When a solvent other than an acid, and in particular an ether, is employed, the operation may be carried out in the presence of a catalyst of the type of those which are used for transesterification reactions. For this purpose, organic nitrogenous bases are used, such as primary, secondary or tertiary amines and heterocyclic bases; representative are diethylamine, ethylamine, triethylamine, n-propylamine, diisopropylamine triethanolamine, pyridine and piperidine. It is also possible to use alkali metal carboxylates, such as K, Li or Na acetates and Lewis acids such as those noted in G. A. Olah, *Friedel-Crafts Reaction*, volume 1, pages 191 to 291. Preferably used are the zinc, titanium, manganese or cobalt salts or metal alkoxides. More preferred are the zinc halides, such as $ZnCl_2$; alkyl titanates, such as methyl, ethyl, n-propyl, isopropyl, n-butyl or isobutyl titanates; Mn and Co carboxylates, such as Mn and Co acetate, propionate and isobutyrate.

The amount of catalyst, expressed in moles per mole of hydroquinone, may range from 0.0001 to 0.2 mole per mole of hydroquinone.

Upon completion of the reaction, the components of the mixture may be separated by distillation and the hydroquinone dicarboxylate and hydroquinone recycled for the preparation of hydroquinone monocarboxylate. When the intention is to prepare monohalohydroquinone monocarboxylates, it is preferable to carry out the halogenation directly on the disproportionation mixture, if need be after having removed the solvent and the disproportionation catalyst. In the case where an alkanoic acid is used as a solvent, the halogenation can take place directly in the disproportionation mixture.

The hydroquinone dicarboxylates employed may be obtained by complete acylation of hydroquinone by means of the usual acylating agents such as acid anhydrides and chlorides.

The process of the invention is very particularly suitable for the preparation of hydroquinone monocarboxylates having the general formula:

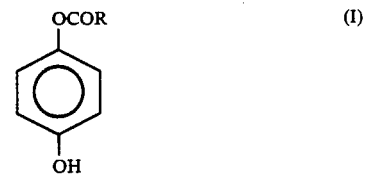

in which R is a straight or branched chain alkyl radical containing from 1 to 4 carbon atoms, from the corresponding hydroquinone dicarboxylates.

Methyl, ethyl, n-propyl, isopropyl, n-butyl and isobutyl radicals are representative of the radicals R.

In order to further illustrate the present invention and the advantages thereof, the following specific examples are given, it being understood that same are intended only as illustrative and in nowise limitative.

EXAMPLE 1

Into a 500 ml glass reactor, equipped with a stirrer and capable of withstanding pressure, were charged:

| | | |
|---|---|---|
| (i) Hydroquinone | 26.4 g | (0.24 mole) |
| (ii) Hydroquinone diacetate | 139.68 g | (0.72 moles) |
| (iii) Diisopropyl ether | 200 ml | |
| (iv) Triethylamine | 1.2 g | (0.012 mole) |

The temperature was raised to 150° C. for 3 hours at autogenous pressure. The solvent and the amine was then stripped off. A light beige solid residue was obtained which weighed 168.9 g. The following compounds were identified and determined by liquid phase chromatography analysis:

| | % by weight in the crude product | Moles | Reactants converted* or formed** |
|---|---|---|---|
| (1) Hydroquinone diacetate | 56.2 | 0.489 | 0.231* |
| (2) Hydroquinone monoacetate | 39.2 | 0.435 | 0.435** |
| (3) Hydroquinone | 1.7 | 0.026 | 0.214* |

Conversion of hydroquinone diacetate: 32.1%
Conversion of hydroquinone: 89.2%
Yield of hydroquinone monoacetate based on consumed hydroquinone and diester thereof: 100%

EXAMPLE 2

Into a 200 ml glass reactor, equipped with a stirring system, thermometer, vertical condenser and heating device, were charged:

| | | |
|---|---|---|
| (i) Hydroquinone | 9.8 g | (0.0891 mole) |
| (ii) Hydroquinone diacetate | 51.8 g | (0.267 mole) |

| (iii) Acetic acid | 246 ml |
| (iv) p-Toluenesulfonic acid | 0.64 g |

The homogeneous mixture was heated at reflux for 3 hours. Acetic acid was then removed by distillation under atmospheric pressure. After cooling a light solid residue was obtained which weighed 32.8 g.

Using liquid phase chromatography analysis, the following compounds were identified and determined:

| (1) Hydroquinone diacetate | 32.8 g | (0.169 mole) |
| (2) Hydroquinone monoacetate | 27.06 g | (0.178 mole) |
| (3) Hydroquinone | 0.96 g | (0.0087 mole) |

The yield of hydroquinone monoacetate was quantitative, based upon the hydroquinone diacetate and hydroquinone reactants which were converted.

EXAMPLE 3

Into a 500 ml glass reactor equipped as in Example 2 were charged:

| (i) Hydroquinone | 8.92 g | (0.081 mole) |
| (ii) Hydroquinone diacetate | 47.18 g | (0.2432 mole) |
| (iii) Acetic acid | 224 ml | |
| (iv) p-Toluenesulfonic acid | 0.58 g | |

The mixture was heated to boiling for 3 hours. The products dissolved in the acetic solution were determined by liquid phase chromatography.

| Compounds | Charged mmoles | Determined, after reaction, mmoles | Converted or formed, mmoles |
| --- | --- | --- | --- |
| (1) Hydroquinone diacetate | 243.2 | 163.6 | 79.6 |
| (2) Hydroquinone monoacetate | | 152.5 | 152.5 |
| (3) Hydroquinone | 81 | 7.9 | 73.1 |

Conversion of hydroquinone: 90.2%
Conversion of hydroquinone diacetate: 32.7%
Yield of hydroquinone monoacetate based on converted hydroquinone and hydroquinone diacetate: 100%.

EXAMPLE 4

Into a 200 ml reactor, equipped with a stirrer and capable of withstanding pressure, were charged:

| (i) Hydroquinone | 11 g | (0.1 mole) |
| (ii) Hydroquinone diacetate | 58.2 g | (0.3 mole) |
| (iii) Acetic acid | 100 ml | |
| (iv) p-Toluenesulfonic acid | 0.5 g | |

The mixture was raised to a temperature of 200° C. under autogenous pressure which was maintained for 2 hours.

The reaction mixture was cooled and diluted with diisopropyl ether. Determination by high pressure chromatography of the ether solution gave the following results:

| (1) Hydroquinone | 1.31 g | (0.012 mole) |
| (2) Hydroquinone diacetate | 39.3 g | (0.203 mole) |
| (3) Hydroquinone monoacetate | 28 g | (0.184 mole) |

Conversion of hydroquinone diacetate: 32%
Yield of hydroquinone monoacetate based on converted hydroquinone diacetate and hydroquinone: 100%.

EXAMPLE 5

The operation was carried out as in Example 1 using carbon tetrachloride instead of diisopropyl ether. The reaction was carried out overnight at 150° C.

The conversion of hydroquinone was 89%.

The yield of monoester was quantitative based upon the converted diester and hydroquinone.

EXAMPLE 6

The operation was carried out as in Example 1 but the solvent was eliminated: the operation took place in the melt at 150° C. without a catalyst.

| (a) Charges: | | |
| --- | --- | --- |
| Hydroquinone | 53 g | (0.482 mole) |
| Hydroquinone diacetate | 291 g | (1.5 mole) |
| (b) Composition of the reaction mixture upon completion of reaction (analysis by high pressure liquid chromatography): | | |
| (1) Hydroquinone | 4.78 g | (0.043 mole) |
| (2) Hydroquinone diacetate | 207 g | (1.07 mole) |
| (3) Hydroquinone monoacetate | 140 g | (0.02 mole) |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a hydroquinone monocarboxylate having the general formula:

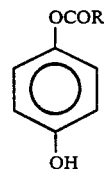

wherein R is a straight or branched chain alkyl radical having from 1 to 4 carbon atoms, comprising disproportionating a stoichiometric excess of a hydroquinone dicarboxylate with hydroquinone.

2. The process as defined by claim 1, comprising carrying out the disproportionation in the presence of a carboxylic acid solvent and a catalytically effective amount of a strong organic or inorganic acid having a pK of less than 1 in water at 25° C.

3. The process as defined by claim 2, comprising carrying out the disproportionation in the presence of from 0.0001 to 0.2 equivalents of strong acid portion per mole of hydroquinone.

4. The process as defined by claim 1, comprising carrying out the disproportionation in the presence of an inert solvent.

5. The process as defined by claim 4, comprising carrying out the disproportionation in the presence of a catalytically effective amount of a transesterification catalyst comprising an organic nitrogenous base, an alkali metal carboxylate or a Lewis acid.

6. The process as defined by claim 4, said inert solvent comprising a carboxylic acid, an ether, a saturated aliphatic, saturated alicyclic or aromatic hydrocarbon, a haloalkane, or a haloaromatic hydrocarbon.

7. The process as defined by claim 6, said inert solvent comprising an alkanoic acid.

8. The process as defined by claim 1, comprising carrying out the disproportionation in the presence of an at least 0.5 mole stoichiometric excess of said hydroquinone dicarboxylate.

9. The process as defined by claim 1, comprising disproportionating at least 1.5 moles of hydroquinone dicarboxlate per mole of hydroquinone.

10. The process as defined by claim 9, comprising disproportionating from 1.5 to 5 moles of hydroquinone dicarboxylate per mole of hydroquinone.

11. The process as defined by claim 1, comprising carrying out the disproportionation at a temperature of from about 50° to 250° C.

* * * * *